United States Patent [19]
Burger et al.

[11] Patent Number: 5,553,626
[45] Date of Patent: Sep. 10, 1996

[54] DEVICE FOR PREVENTING BRUXISM

[76] Inventors: Michael A. Burger, Pasqualinistraat S, 5622 AW Eindhoven; Rigobertus W. Martens, Schweitzerlaan 2S, 5644 DL Eindhoven, both of Netherlands

[21] Appl. No.: 382,000

[22] PCT Filed: Jun. 9, 1994

[86] PCT No.: PCT/NL94/00133
  § 371 Date: Feb. 9, 1995
  § 102(e) Date: Feb. 9, 1995

[87] PCT Pub. No.: WO94/28828
  PCT Pub. Date: Dec. 22, 1994

[51] Int. Cl.⁶ ................................ A61B 5/103
[52] U.S. Cl. .................. 128/777; 128/774; 607/2
[58] Field of Search ................. 128/772, 782, 128/774, 777; 607/2, 6, 47, 48

[56] References Cited

U.S. PATENT DOCUMENTS

| | | |
|---|---|---|
| 4,669,477 | 6/1987 | Ober ........................... 128/777 X |
| 4,842,519 | 6/1989 | Dworkin ...................... 128/777 X |
| 4,934,378 | 6/1990 | Perry, Jr. ..................... 128/777 X |
| 4,976,618 | 12/1990 | Anderson ................... 128/777 X |
| 4,979,516 | 12/1990 | Abraham, II ............... 128/777 |
| 4,989,616 | 2/1991 | Lee, Jr. ........................ 128/777 |
| 4,995,404 | 2/1991 | Nemir . |
| 5,078,153 | 1/1992 | Nordlander . |
| 5,190,051 | 3/1993 | Wilson . |
| 5,212,476 | 5/1993 | Maloney ...................... 128/777 X |

*Primary Examiner*—Sam Rimell
*Attorney, Agent, or Firm*—Frishauf, Holtz, Goodman, Langer & Chick

[57] ABSTRACT

An anti bruxism device for stopping or at least diminishing bruxism comprises a splint adapted to be secured to a tooth of a user, and a biofeedback system mounted on the splint. The biofeedback system includes a detector for detecting bruxism, and a stimulation device for stimulating the user responsive to detection of bruxism by the detector. The stimulation produced by the stimulation device causes the user to stop bruxating. Bruxism is a function that could damage teeth and molars, and may affect the neuro-muscular system in a negative way, and could cause, for example, headaches.

14 Claims, 1 Drawing Sheet

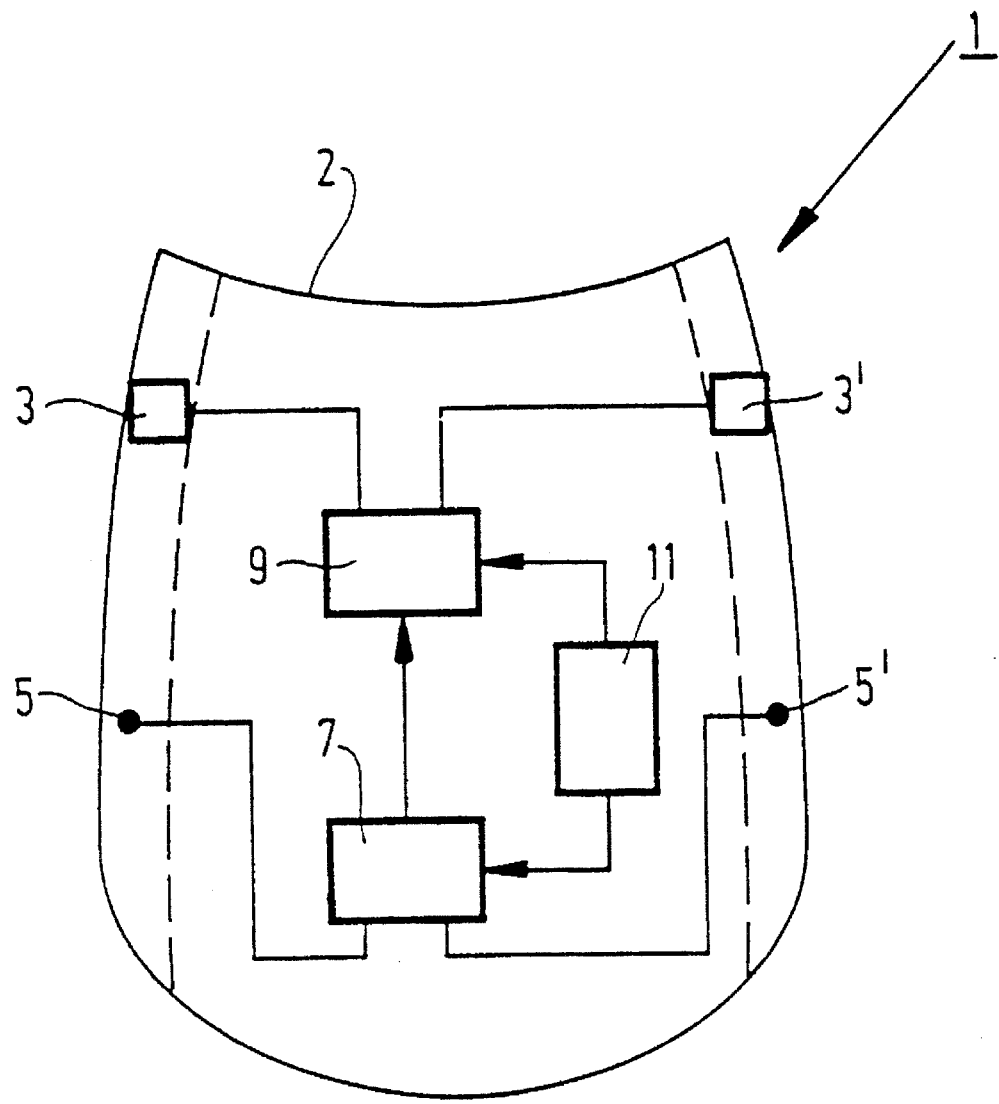
FIG.

DEVICE FOR PREVENTING BRUXISM

BACKGROUND OF THE INVENTION

The invention concerns an anti-bruxism device. Bruxism is a conscious or subconscious parafunction that takes place during the day and/or at night, and consists of a static and/or dynamic contact between the chewing levels of the mandibular and upper jaw.

Herewith appears an avowed neuro-muscular activity. These contacts are not physiological. Bruxism, also known as teeth-grinding or teeth-jamming, has two consequences concerning ones health. First it damages the teeth and molars, and secondly it influences the neuro-muscular system negatively. (muscle spasms, arthrosis, etc.)

The purpose of the invention is to develop a device that stops bruxism and raises the hurtful accesories. The device consists of an already used splint (synthetic resin) as carrier for a special biofeedback system. A splint is a synthetic resin modelled plate most frequently worn on the teeth of the upper jaw.

The biofeedback system detects bruxism, transponds a signal which diminishes, and finally stops bruxism. This device can also be used for preventive means; that is to say with patients grinding their teeth who don't yet suffer the consequences.

A prototype example of the anti-bruxism device features a biofeedback system with at least one pressure sensor, connected to a transponding element (e.g. a chip), which is connected to a pulse generator.

This generator transmits a, preferably, electrical impulse to a conducting splint anchor.

In this example the splint is worn on the palate of the mouth, in which the pressure sensors (in the synthetic resin) are extended over the upper jaw teeth.

When bruxism occurs, the pressure sensor measures the pressure force between teeth and/or molars and signals the transponding unit, in case the pressure force reaches a previous adjusted value or time, and another signal is given to the pulse generator in a way an (e.g.) electrical impulse irritates the molar region via the anchor.

By this, the patient receives a stimulation through which the bruxism stops (reflex activity).

If worn, during the sleep, this sleep may not be interrupted.

BRIEF DESCRIPTION OF THE DRAWINGS

The single FIGURE shows a simple example of an Anti-bruxism device.

DETAILED DESCRIPTION

The main elements of the device of the present invention are:
-1-Anti-bruxism device according to the present invention.
-2-Splint. The splint is worn against the palatum, and contains the biofeedback system. The splint is a copy of the palatum and upper jaw teeth. In this example the splint is attached to two conducting anchors.
-3-, -3'-The anchors. The anchors have a twofold purpose, namely to fix the splint, and to conduct the electrical impulses.
-5-,-5'-Pressure sensors.
-7-Pressure registration element. This is attached to pressure sensors and signals, as written above, the pulse generator.
-9-Pulse generator. This generator conducts the (electrical) impulse to the anchors. The developped irritation stops bruxism without disturbing normal biological functions as for example sleep and intra oral pH.

The pulses, received by the anchors are preferably electric. As an alternative, thermical or vibrating pulses could be used.

The way in which the mechanical pressure will be conducted in an electrical impulse can be various, dependent on the technical possibilities, for example: piezeoelectric material, electrodes in plastic, chip, etc.

The anchors,-3-,-3'-, are made from currently used orthodontical conducting metal.

The connections between the separate elements of the biofeedback system should be prepared into the synthetic resin, so the splint is an insulator.

A battery 11 provides the necessary voltage for pressure measuring, and to conduct the impulses.

A Wheatstone bridge and condensator could be integrated in the system.

All material used should be biocomatible.

The anti-bruxism device will preferably be worn during nighttime. The user will be reacting unconsciously, (the sleep should not be disturbed) and stops bruxating (reflex activity).

It's obvious that the device can be manufactured in several ways depending on the details, without deviating from the essence of the invention.

We claim:

1. An anti-bruxism device, comprising:
   a splint adapted to be secured to a tooth of a user; and
   a biofeedback system mounted on said splint, said biofeedback system including;
      a detector for detecting bruxism; and
      a stimulation device for stimulating the user responsive to detection of bruxism by said detector, said stimulation device including at least one splint anchor mounted on said splint for conducting said stimulation to the user;
      whereby said stimulation by said stimulation device causes the user to stop bruxating.

2. The anti-bruxism device of claim 1, wherein: said detector includes:
   at least one pressure sensor coupled to said splint; and
   a pressure registration element coupled to said at least one pressure sensor; and said stimulation device further includes:
   a pulse generator coupled to said pressure registration element for producing pulses responsive to an output of said pressure registration element; and
   wherein said at least one splint anchor includes means for conducting said pulses to the user to stimulate the user responsive to detection of bruxism by said detector.

3. The anti-bruxism device of claim 2, wherein said stimulation device comprises two of said splint anchors, and wherein said splint anchors are made of electrically conducting material.

4. The anti-bruxism device of claim 2, wherein said biofeedback system further includes an electrical power source mounted on said splint and coupled to said pressure registration element and to said pulse generator.

5. The anti-bruxism device of claim 2, wherein said pulse generator includes means for generating electrical pulses.

6. The anti-bruxism device of claim 5, wherein said splint is made of an electrically insulating material.

7. The anti-bruxism device of claim 6, wherein said electrically insulating material is a synthetic resin material.

8. The anti-bruxism device of claim 2, wherein said splint is made of an electrically insulating material.

9. The anti-bruxism device of claim 2, wherein said electrically insulating material is a synthetic resin material.

10. The anti-bruxism device of claim 1, wherein said biofeedback system further includes an electrical power source mounted on said splint and coupled at least to said stimulation device to power said stimulation device.

11. The anti-bruxism device of claim 1, wherein said at least one splint anchor further includes means for fixing said splint in the mouth of the user.

12. The anti-bruxism device of claim 11, wherein said at least one splint anchor further includes means for conducting said stimulation to the tooth of a user.

13. The anti-bruxism device of claim 2, wherein said pulse generator includes means for generating thermical pulses.

14. The anti-bruxism device of claim 2, wherein said pulse generator includes means for generating vibrating pulses.

* * * * *